United States Patent [19]

Johnson, et al.

[11] Patent Number: 4,685,072
[45] Date of Patent: Aug. 4, 1987

[54] STEAM GENERATOR ON-LINE EFFICIENCY MONITOR

[75] Inventors: Ralph K. Johnson, Highland Heights; Azmi Kaya, Akron; Marion A. Keyes, IV, Chagrin Falls, all of Ohio; William H. Moss, Kingwood, Tex.

[73] Assignee: The Babcock & Wilcox Company, New Orleans, La.

[21] Appl. No.: 688,213

[22] Filed: Jan. 2, 1985

Related U.S. Application Data

[63] Continuation-in-part of Ser. No. 329,538, Dec. 10, 1981, abandoned.

[51] Int. Cl.⁴ ............... G06F 15/46; G06F 15/36; F23N 5/18
[52] U.S. Cl. .................... 364/551; 60/665; 236/15 E; 431/76
[58] Field of Search ............ 364/550, 551, 492, 494; 122/448 B, 448 R; 431/76; 60/665; 73/112; 236/15 R, 15 E

[56] References Cited

U.S. PATENT DOCUMENTS

| | | | |
|---|---|---|---|
| 1,591,444 | 7/1926 | Stein | 236/15 E |
| 2,723,559 | 11/1955 | Germer | 73/112 |
| 4,069,675 | 1/1978 | Adler et al. | 364/492 X |
| 4,362,499 | 12/1982 | Nethery | 431/76 X |
| 4,418,541 | 12/1983 | Russel | 122/448 B |
| 4,435,650 | 3/1984 | Dziubakowski et al. | 307/32 |
| 4,509,912 | 4/1985 | Van Berkum | 431/76 |
| 4,557,686 | 12/1985 | Laspisa | 122/448 B |
| 4,575,334 | 3/1986 | Keyes, IV et al. | 431/76 |
| 4,576,570 | 3/1986 | Adams et al. | 431/76 X |
| 4,583,497 | 4/1986 | Likins, Jr. et al. | 122/448 B |

FOREIGN PATENT DOCUMENTS

| | | | |
|---|---|---|---|
| 510525 | 7/1939 | United Kingdom . | |
| 1561020 | 2/1980 | United Kingdom | 431/76 |
| 1562536 | 3/1980 | United Kingdom | 431/76 |

OTHER PUBLICATIONS

Faires et al: Thermodynamics (Textbook) MacMillan Publishing Co. Copyright 1978 pp. 47, 61, 198, 350 and 351 of interest.
Campbell: Thermodynamic Analysis of Combustion Engines, John Wiley and Sons (Textbook) Copyright 1979 pp. 239–248 of interest.

*Primary Examiner*—Felix D. Gruber
*Attorney, Agent, or Firm*—Vytas R. Matas; Robert J. Edwards

[57] ABSTRACT

A system for the automatic and continuous determination of the efficiency of a fossil fuel-fired vapor generator for utilization by an automatic load control (88) to control the distribution of the system load among a plurality of generators, wherein various heat losses from various combustion sources are separately determined, the individual losses summed (80) and subtracted (86) from 100 percent to obtain a measure of the vapor generator efficiency.

7 Claims, 1 Drawing Figure

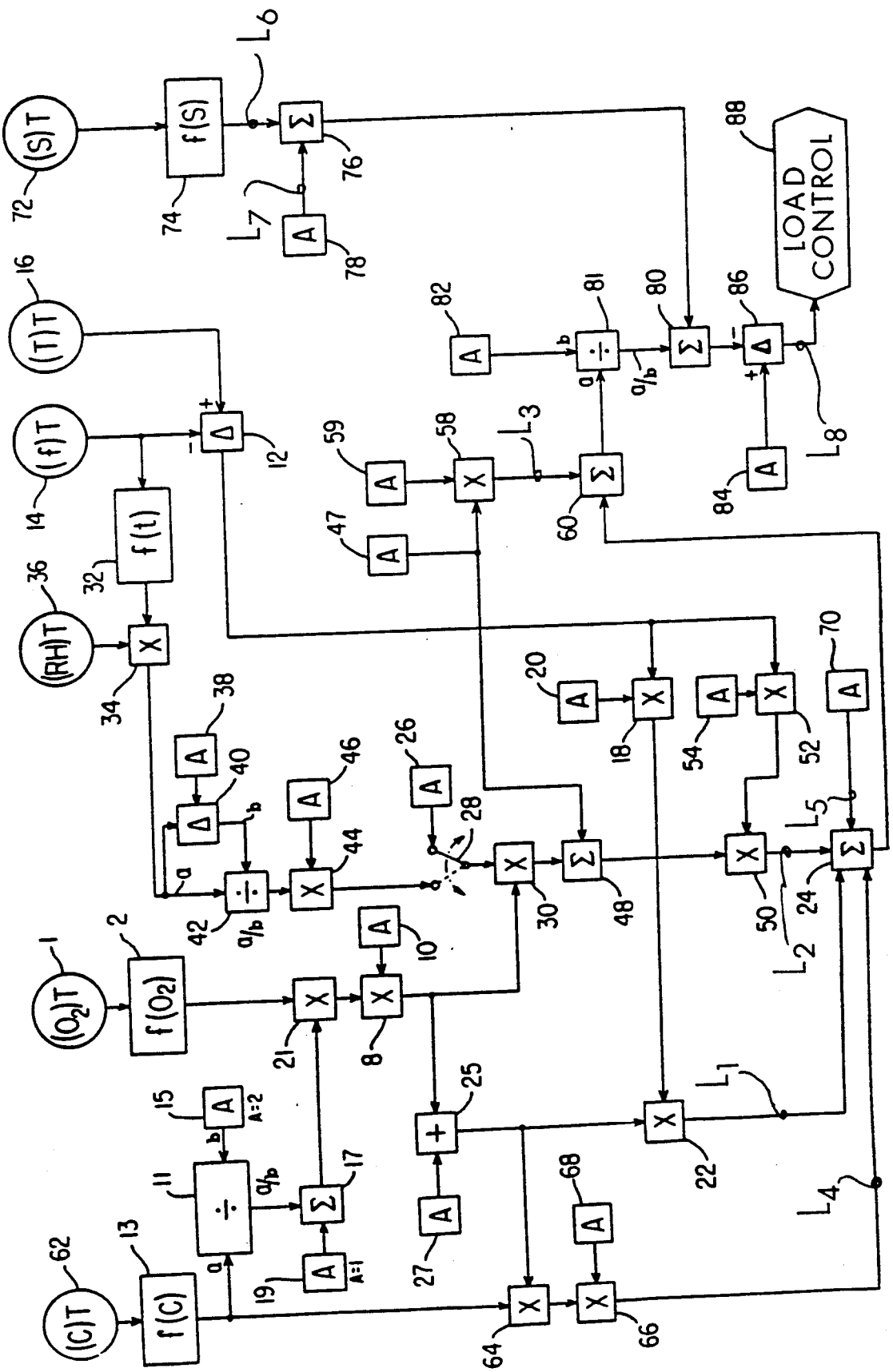

STEAM GENERATOR ON-LINE EFFICIENCY MONITOR

This is a continuation-in-part of application Ser. No. 329,538, filed Dec. 10, 1981 and now abandoned.

TECHNICAL FIELD

This invention relates to a system for automatically and continuously monitoring the efficiency of a fossil fuel-fired steam generator for utilization by an automatic load control which controls the distribution of the system load among a plurality of generators.

BACKGROUND ART

Boiler efficiency calculation methods are useful for determining which operating methods will reduce the amount of fuel required. Because there are many variations in the combustion process and many control settings available to meet steam demands, some type of efficiency calculation is necessary.

An on-line efficiency calculation is desirable due to the fact that the combustion process is highly variable with constant changes in load demand and gradual, long term changes in burner equipment efficiency and ambient atmospheric conditions.

Fuel heating value can also vary for fuels such as bark, refuse, blast furnace gas, residue oils, waste sludge, or blends of coal. As a result, control settings, based on steady state calculations of boiler efficiency using average daily or weekly fuel/air and fuel heating values, may not result in the most economical operation of the boiler.

For systems with multiple boilers, operating costs may be reduced thru the use of boiler management optimization and load allocation systems. Boiler management systems set the fuel firing to the various boilers to minimize fuel costs. Some reliable measurement of boiler efficiency is required with these systems to obtain maximum fuel savings.

One technique for determining the efficiency of a fossil fuel-fired steam generator, as set forth in the ASME/ANSI Power Test Codes, is the so-called Heat Loss Method which is based on the calculation of heat losses per pound of fuel. The generator efficiency is then the difference between the higher heating value of the fuel minus the total of the calculated heat losses, expressed in percent, for given feedwater conditions.

A complete efficiency test of a fossil fuel-fired steam generator as presently conducted requires many man-hours of labor to record the required data at stipulated increments of time over an extended period of time and then to make the necessary calculations at each of several loads. Furthermore, to obtain meaningful results, during the period of time in which the tests are conducted, the generator must be held in a steady-state condition. For these reasons efficiency tests are usually conducted only when required to meet performance guarantees.

Bonne et. al. (GF Pat. No. 2,016,707 A) recites a flue gas loss or combustion efficiency meter primarily for use in furnaces using natural gas. Compensation is not made for losses due to incomplete combustion, radiation, air leaks, blowdown, moisture in the air, and unburned carbon in the ash. The present invention compensates for all of these losses and results in a system capable of measuring the boiler efficiency of a furnace utilizing most fuels including coal, oil, natural gas, hydrogen, etc.

With the foregoing in mind it is the principal objective of this invention to provide a system whereby the efficiency of a fossil fuel-fired steam generator is automatically and continuously monitored and is utilized by an automatic load control, such as described in U.S. Pat. No, 4,435,650, to control the distribution of the system load among a plurality of generators. This and further objectives of the invention will be apparent as the description proceeds in connection with the drawings in which:

IN THE DRAWING

The drawing is a logic diagram of a system embodying the principles of this invention.

DETAILED DESCRIPTION

In the drawing conventional logic symbols have been used. It will be recognized that the components, or hardware, as it is sometimes called, which such symbols represent are commercially available and their operation well understood by those familiar with the art. Further, conventional logic symbols have been used to avoid specific identification of this invention with any particular type of components such as analog or digital, as this invention comprehends either one or a combination of such types.

Referring now to the drawing, excess air in the flue gas is determined by means of an oxygen transducer 1, generating a signal transmitted to a function generator 2, the output signal from which is proportional to the total air supplied for combustion in percent by weight. There is a substantially constant relationship between oxygen content in the flue gas and total air regardless of the fuel being burned, particularly as in modern steam generators the excess air can be maintained at low values in the order of 20 percent or less. If required, however, the output signal from the function generator 2 may be adjusted to compensate for changes in the proportionality between oxygen content in the flue gas and total air occasioned by a change in fuel.

A signal proportional to the pounds of air supplied for combustion per pound of fuel is obtained by multiplying, in a multiplying unit 8, the signal from the function generator 2, by a signal proportional to the theoretical air required in pounds per pound of fuel, generated in a manually adjustable unit 10.

Oxygen analyzers of the so-called electrochemical type using a Zirconium-oxide sensor operate at approximately 1500° F. At this temperature unburned combustibles, such as CO and $H_2$ react with the oxygen present in the flue gas. As a result, the signal generated by the oxygen transducer 1 is proportional to the excess oxygen remaining in the flue gas based on complete combustion. If such an oxygen transducer is incorporated in the system, a correction to the output signal from the function generator 2 is made by dividing in half, by means of a divider unit 11 and a signal generator 15, the output signal from a function generator 13 responsive to the signal generated in a combustibles transducer 62.

The output signal from divider unit 11 is then summed in a summing unit 17 with a constant value signal generated in signal generator 19. The output signal from function generator 2 is then multipled in a multiplier unit 21 producing an output signal proportional to the pounds of dry air in pounds per pound of fuel. If the oxygen transducer is of a type having an operating temperature below the temperature at which the unburned combustibles react with the oxygen present in the flue gas, such as the so-called catalytic combustion or paramagnetic types, then no such correction is required.

The pounds of dry exit flue gas per pound of fuel is obtained by adding, in an adder unit 25, to the output signal from multiplier unit 8 a signal proportional to the weight of combustibles in a pound of fuel generated in a signal generator 27.

Having thus obtained the pounds of dry air and pounds of dry flue gas per pound of fuel, the individual losses due to heat in the exit flue gas, moisture in the air supplied for combustion, sensible and latent heat in the $H_2O$ in the fuel and combustibles in the flue gas (if any) are determined as follows:

Heat Loss in Dry Flue Gas (BTU/lb. of Fuel)

$$L_1 = \text{(Pounds Dry Flue Gas/Pound of Fuel)} (0.247) (T-t) \quad (1)$$

Where:
$L_1$ = Heat Loss in dry flue gas in BTU/lb. Fuel
T = Flue Gas Temperature °F.
t = Ambient Temperature °F.
0.247 = Sp. Ht. dry air BTU/(lb.-°F.) at 14.7 PSIA
It has been assumed that the specific heats of the dry flue gas is very nearly equal to the specific heat of dry air.

A signal proportional to the difference in ambient and exit flue gas temperatures is generated in a difference unit 12 responsive to the output signal from an ambient temperature transducer 14 and a flue gas exit temperature transducer 16. The signal generated in difference unit 12 is then multiplied in a multiplying unit 18 by the output signal from a signal generator 20 proportional to the specific heat of the dry flue gas. To obtain a signal proportional to the heat loss in the exit dry flue gas per pound of fuel the output signal from multiplying unit 18 is multiplied in a multiplying unit 22 by the output signal from adder unit 25. The output signal from multiplying unit 22 forms one input to a loss summing unit 24.

Sensible Heat Loss Due to Moisture in the Combustion Air & Fuel $$L_2 = \{((\text{lbs. dry air/lb. fuel})(y)) + \text{lbs. Moist. in lb. of fuel}\}(\text{Sp. Ht. of } H_2O)(T - t)$$

Where:
$L_2$ = Sensible heat loss due to moisture in air & fuel
y = Moisture in combustion air lbs./lb. of combustion air Conveniently, $L_2$ can be determined by first determining the total moisture in the combustion air and fuel, then determining the heat loss per pound of moisture, the product of the two determinations being the sensible heat loss $L_2$.

The amount of moisture in the combustion air is often taken as y = 0.013 pounds per pound of dry air, corresponding to conditions of 80° F. ambient temperature and 60 percent relative humidity; or y can be calculated from measurements of ambient air temperature and relative humidity for varying weather conditions.

When moisture is assumed to be 0.013 pounds per pound of dry air, a signal proportional thereto is generated in a signal generator 26, transmitted through a selector switch 28 to a multiplying unit 30 for multiplication by the output signal from multiplier unit 8 to produce a signal proportional to the pounds of moisture in the pounds of combustion air per pound of fuel.

When moisture is calculated from measurements of ambient air temperature and relative humidity, a signal proportional to the vapor pressure of $H_2O$ at ambient temperature is first generated by means of a function generator 32 responsive to the signal generated in ambient temperature transducer 14, which is multiplied in a multiplier unit 34 by a signal proportional to the relative humidity of the ambient air supplied for combustion, generated in a relative humidity transducer 36. The output signal from multiplier unit 34 is then modified in accordance with changes in atmospheric pressure by means of a signal generator 38 generating a signal corresponding to ambient pressure which is subtracted from the output signal (a) from multiplying unit 34 in a difference unit 40 producing an output signal (b) by which the output signal (a) is divided in a divider unit 42. The output signal from the divider unit 42 is then multiplied, in a multiplier unit 44, by a signal corresponding to the ratio between the molecular weight of water vapor and air, generated in a signal generator 46, to produce a signal proportional to the pounds of water vapor per pound of air supplied for combustion. This signal may then be transmitted through selector switch 28 to multiplier unit 30 to produce the signal proportional to the pounds of moisture in the pounds of combustion air per pound of fuel.

A signal proportional to the pounds of moisture in a pound of fuel is generated in a signal generator 47 and transmitted to a summing unit 48 wherein it is added to the signal from multiplying unit 30 to produce an output signal proportional to the total moisture in the combustion air and fuel per pound of fuel. This output signal is then multiplied in a multiplier unit 50 by a signal proportional to the heat in BTU wasted in the flue gases per pound of moisture to produce a signal proportional to the total loss per pound of fuel which is transmitted to loss summing unit 24. The heat wasted in the flue gases per pound of moisture is obtained by multiplying the signal from difference unit 12 in a multiplier unit 52 by a signal proportional to the specific heat of water vapor, usually taken as 0.475 BTU per pound per degree, generated in a signal generator 54.

Heat Loss Due to Vaporization of Water in the Fuel $$L_3 = (\text{lbs. water in fuel/lb. of fuel}) (1049) \quad (3)$$

Where:
$L_3$ = Heat loss due to vaporization of water in the fuel
1049 = Latent heat of vaporization BTU/lb. of water
The signal proportional to the moisture in the fuel, generated in signal generator 47 is multiplied, in a multiplier unit 58, by a signal proportional to the heat of vaporization (assumed to be 1049 BTU/lb. of water) generated in a second generator 59. The output signal from multiplier unit 58 is transmitted to a loss summing unit 60.

Heat Loss Due to Unburned Combustibles in the Flue Gas $$L_4 = (\% \text{ combustibles in the flue gas}) (\text{lbs. dry flue gas/lb. of fuel}) (9,746) \quad (4)$$

Where:

$L_4$ = Loss due to Unburned Combustibles
9746 = Heat of Combustion BTU/lb. CO to $CO_2$ While by good design and careful operation no unburned gaseous combustibles will be found in the flue gases, under certain conditions they may be unavoidable. The usual gaseous combustible is CO which, if present, materially reduces steam generator efficiency. This loss in BTU per pound of fuel is determined by means of the transducer 62 and function generator 13 generating a signal proportional to the percent combustibles present in the flue gas which is multiplied, in multiplier unit 64 by the output signal from adder unit 25 to obtain a signal proportional to the pounds of CO per pound of fuel. The output signal from multiplier 64 is then multiplied, in a multiplier unit 66, by the output signal from a signal generator 68 proportional to the heat of combustion of CO to $CO_2$ which is 9,746 BTU per pound of CO. The signal from multiplier unit 66, proportional to the BTU loss per pound of fuel forms one input signal to loss summing unit 24.

Heat Loss Due to Unburned Carbon in the Ash $$L_5 = (\text{lbs. ash/lb. fuel}) \frac{(\text{lbs. carbon/lb. ash})}{(1 - \text{lbs. carbon/lb. ash})} (14,500)$$

Where: $L_5$ = loss in BTU/lb. of fuel due to carbon in the ash 14,500 — heat of combustion, carbon to carbon dioxide This calculation requires an analysis of the ash to determine the pounds of carbon in the ash per pound of ash. The loss in BTU per pound of fuel is then determined by means of equation (5). As shown in the drawing, a signal proportional to the loss is generated in a signal generator 70 which is transmitted to loss summing unit 24.

Heat Loss Due to Heat Radiation $$L_6 = (K)((Fractional\ Load)^{-0.95}) \quad (6)$$

Where:
$L_6$ = Radiation loss in percent of heat input
K = A constant

The heat loss due to radiation varies inversely in nonlinear functional relationship to generator load as expressed in equation (6). As shown in the drawing, a signal proportional to the fractional boiler load is generated in a steam flow transducer 72 and a signal proportional to the non-linear functional relationship between fractional load and radiation loss is generated in function generator 74.

Unaccounted for Losses $L_7$ = Unaccounted for losses in percent of heat input

In addition to the loss due to heat radiation, there are certain other losses due, for example, to heat leaks and blow down. These losses are based on experiences reported in the literature and are expressed as percent losses and accordingly may be added to the signal output of function generator 74 by means of a summing unit 76. A signal generated in signal generator 78 inputs to summing unit 76 to produce an output signal proportional to the total of radiation and unaccounted for losses in percent which is transmitted to a summing unit 80.

Determination of Vapor Generator Efficiency $$L_8 = 100 = \left\{ \left( \left( \frac{(L_1 + L_2 + L_3 + L_4 + L_5)\text{BTU/lb. of fuel}}{\text{Heat value of the fuel BTU/lb. of fuel}} \right)(100) \right) + L_6 + L_7 \right\}$$

Where: $L_8$ = Boiler efficiency in percent of heat input

The losses summed in summing unit 60, expressed in BTU per pound of fuel, are converted to losses in percent by dividing the output signal from summing unit 60 in a divider unit 81, by a signal proportional to the higher heating value of the fuel generated in a signal generator 82, to produce a signal proportional to the losses summed in summing unit 60 expressed in percent. The output signal from divider unit 81 is then summed in summing unit 80 with the signal from summing unit 76 to obtain an output signal proportional to the total percent losses, which is converted to a signal proportional to boiler efficiency by subtracting the output signal, in a difference unit 86 from the signal having a constant value of 100, generated in a signal generator 84. The output signal from difference unit 86 is transmitted to an automatic load control, schematically illustrated at 88 such as described in U.S. Pat. No. 4,435,650, to control the system load along a plurality of generators.

We claim:

1. A system for automatically and continuously determining the efficiency of a combustion process in a fossil-fuel fired vapor generator for utilization by an automatic load control system that controls the distribution of a system load among a plurality of vapor generators, comprising:

a first function generator, connected to an oxygen transducer for sensing the level of excess air in the flue gas, for generating a first signal indicative of the total air supplied for combustion in percent by weight;

a second function generator, connected to a combustibles transducer for sensing the level of combustibles in the flue gas, for generating a second signal indicative of the percent combustibles present in the flue gas;

means for correcting the first signal, connected to said first and second function generators, when the oxygen transducer is of a type that operates at a temperature level sufficient to cause the unburned combustibles to react with the oxygen present in the flue gas;

an ambient air temperature transducer for generating a third signal indicatve of the temperature of the ambient air supplied to the vapor generator for combustion;

a flue gas exit temperature transducer for generating a fourth signal indicative of the temperature of the flue gas exiting from the vapor generator;

means for generating a fifth signal indicative of the temperature difference between the flue gas exiting from the vapor generator and the ambient air supplied to the vapor generator;

means for generating a sixth signal indicative of the specific heat of the dry flue gas;

means for generating a ninth signal, indicative of the pounds of dry exit flue gas per pound of fuel, from said first and second signals, a seventh signal indicative of the required theoretical air for combustion, and an eighth signal indicative of the weight of combustibles in a pound of fuel; and means for generating a tenth signal, indicative of the heat loss in dry flue gas, from the product of said fifth, and sixth and ninth signals.

2. The system as set forth in claim 1 further including a third function generator, connected to a rate of steam flow transducer for sensing the rate of vapor flow in the vapor generator, for generating an eleventh signal indicative of the heat loss from the vapor generator due to radiation, in percent of heat input.

3. The system as set forth in claim 2 further including means for generating a twelfth signal indicative of the amount of moisture in the combustion air, under actual or assumed conditions, and comprised of:

(a) a signal generator for generating a thirteenth signal indicative of a value of 0.013 pounds of moisture per pound of dry air under assumed conditions;

(b) means for generating a fourteenth signal indicative of the amount of moisture in the combustion air under actual conditions including:
  (i) a fourth function generator, connected to said ambient temperature transducer, for generating a signal indicative of the vapor pressure of water at ambient temperature;
  (ii) a relative humidity transducer, connected to said fourth function generator, for generating a sixteenth signal indicative of the relative humidity of the ambient air supplied for combustion;
  (iii) means for generating a seventeenth signal equal to the product of said fiteenth and sixteenth signals;
  (iv) means for modifying the seventeenth signal to account for changes in atmospheric pressure to obtain an eighteenth signal;
  (v) means for multiplying the eighteenth signal by a ratio between the molecular weight of water vapor and air to obtain said fourteenth signal; and (c) a selector switch, connected to said signal generator and to said means for generating the fourteenth signal for selecting either the thirteenth or fourteenth signals.

4. The system as set forth in claim 3 further including:
means for generating a nineteenth signal, equal to the product of said corrected first signal and said seventh signal, indicative of the pounds of dry air per pound of fuel;

means for generating a twentieth signal, equal to the product of said nineteenth and twelfth signals, indicative of the pounds of moisture in the pounds of combustion air per pound of fuel;

means for generating a twenty-first signal indicative of the pounds of moisture per pound of fuel;

means for generating a twenty-second signal indicative of the specific heat of water vapor; and means for generating a twenty-third signal indictaive of the sensible heat loss due to moisture in the combustion air and fuel from the sum of said twentieth and twenty-first signals multiplied by said fifth and by said twenty-second signals.

5. The system as set forth in claim 4 further including:

means for generating a twenty-fourth signal indicative of the latent heat of vaporization of water;

means for generating a twenty-fifth signal, equal to the product of said twenty-first and twenty-fourth signals, indicative of the heat loss due to vaporization of water in the fuel;

means for generating a twenty-sixth signal indicative of the heat loss due to unburned carbon in the ash; and means for generating a twenty-seventh signal indicative of the unaccounted for losses.

6. The system as set forth in claim 5 further including:

means for generating a twenty-eigth signal indicative of the heat of combustion of CO to $CO_2$;

means for generating a twenty-ninth signal, equal to the product of said second, ninth and twenty-eighth signals, indicative of the heat loss due to unburned combustibles in the flyash;

means for generating a thirtieth signal, equal to the sum of said tenth, twenty-third, twenty-fifth, twenty-sixth, and twenty-ninth signals;

means for generating a thirty-first signal, indicative of the higher heating value of the fuel;

means for generating a thirty-second signal, equal to the quotient of the thirtieth signal divided by the thirty-first signal;

means for generating a thirty-third signal, equal to the sum of said eleventh and twenty-seventh signals, indicative of the sum of the radiation and unaccounted for losses in percent; and means for generating a thirty-fourth signal, equal to the sum of said thirty-second and thirty-third signals subtracted from 100, indicative of the vapor generator efficiency in percent of heat input.

7. A method for the automatic and continuous determination of a vapor generator efficiency for utilization by an automatic load control comprising the steps of:

generating a first signal proportional to the pounds of dry exit flue gas per pound of fuel;

generating a second signal corresponding to the temperature difference between the sensed exit flue gas and the sensed air supplied combustion;

generating a third signal proportional to the specific heat of the dry exit flue gases;

generating a fourth signal proportional to the product of the first, second, and third signals and to the heat loss in the dry flue gas in BTU per pound of fuel;

generating a fifth signal proportional to the pounds of combustibles in the exit flue gas per pound of fuel;

generating a sixth signal proportional to the heat of combustion of said combustibles;

generating a seventh signal proportional to the product of said fifth and sixth signals and to the heat loss due to combustibles in the exit flue gas in BTU per pound of fuel;

generating an eighth signal proportional to the pounds of moisture in the air supplied for combustion per pound of fuel;

generating a ninth signal proportional to the pounds of moisture in the fuel per pound of fuel;

generating a tenth signal proportional to the sum of said eighth and ninth signals;

generating an eleventh signal proportional to the specific heat of water vapor;

generating a twelfth signal proportional to the product of said second and eleventh signals;

generating a thirteenth signal proportional to the product of said tenth and twelfth signals and to the heat loss due to moisture in the fuel and air supplied combustion per pound of fuel;

generating a fourteenth signal proportional to the latent heat of vaporization of the water in the fuel;

generating a fifteenth signal proportional to the product of the ninth and fourteenth signals and to the latent heat of vaporization of the water in the fuel;

generating a sixteenth signal proportional to the rate of vapor flow from the generator;

generating a seventeenth signal varying in inverse non-linear relationship to the magnitude of said sixteenth signal and to the heat loss in percent due to heat radiation from the vapor generator;

generating an eighteenth signal proportional to the loss due to unburned carbon in the fuel ash in BTU per pound of fuel;

generating a nineteenth signal proportional to the heat loss in percent due to unaccounted for losses;

generating a twentieth signal proportional to the sum of the fourth, seventh, thirteenth, fifteenth, and eighteenth signals;

generating a twenty-first signal proportional to the higher heating value of fuel;

generating a twenty-second signal proportional to the twentieth signal divided by the twenty-first signal;

generating a twenty-third signal proportional to the sum of the seventeenth, nineteenth, and twenty-second signals and to the total of the said heat losses in percent;

generating a twenty-forth signal proportional to 100 percent efficiency of the vapor generator; and generating a twenty-fifth signal proportional to difference between said twenty-forth signal and twenty-third signals and to the vapor generator efficiency.

* * * * *